US008834443B2

(12) United States Patent
Yeung

(10) Patent No.: US 8,834,443 B2
(45) Date of Patent: Sep. 16, 2014

(54) INJECTION SAFETY SYSTEM

(75) Inventor: Alex Yeung, Toronto (CA)

(73) Assignees: Alex Yeung, Toronto, Ontario (CA); MJ & AJ Holdings Ltd., Richmond Hill, Ontario (CA)

( * ) Notice: Subject to any disclaimer, the term of this patent is extended or adjusted under 35 U.S.C. 154(b) by 0 days.

(21) Appl. No.: 13/636,400

(22) PCT Filed: Mar. 21, 2011

(86) PCT No.: PCT/CA2011/000292
§ 371 (c)(1),
(2), (4) Date: Sep. 21, 2012

(87) PCT Pub. No.: WO2011/116462
PCT Pub. Date: Sep. 29, 2011

(65) Prior Publication Data
US 2013/0012908 A1  Jan. 10, 2013

Related U.S. Application Data

(60) Provisional application No. 61/316,088, filed on Mar. 22, 2010.

(51) Int. Cl.
A61B 19/00 (2006.01)
B65D 51/00 (2006.01)
A61J 1/20 (2006.01)
G09F 3/04 (2006.01)
B65D 51/24 (2006.01)
A61J 1/18 (2006.01)
G09F 3/02 (2006.01)
A61J 1/14 (2006.01)

(52) U.S. Cl.
CPC ............... *G09F 3/04* (2013.01); *B65D 51/002* (2013.01); *A61J 1/2096* (2013.01); *B65D 51/245* (2013.01); *A61M 2205/60* (2013.01); *A61J 1/18* (2013.01); *G09F 2003/0273* (2013.01); *A61J 2001/1487* (2013.01); *A61M 2205/6081* (2013.01); *A61J 1/1412* (2013.01); *G09F 2003/023* (2013.01); *A61J 2205/00* (2013.01)
USPC .......................................................... 604/404

(58) Field of Classification Search
USPC ........ 604/66, 68, 193.01, 232, 403–416, 500, 604/506; 221/199, 282
See application file for complete search history.

(56) References Cited

U.S. PATENT DOCUMENTS

| 4,921,277 A | * | 5/1990 | McDonough ................ 283/81 |
| 5,284,263 A | * | 2/1994 | Papciak .................... 215/230 |
| 5,692,640 A | * | 12/1997 | Caulfield et al. .............. 221/70 |
| 6,985,870 B2 | | 1/2006 | Martucci et al. |
| 2004/0243434 A1 | | 12/2004 | Peterka et al. |

FOREIGN PATENT DOCUMENTS

| CA | 2188087 A1 | 4/1997 |
| CA | 2255507 A1 | 6/2000 |

* cited by examiner

*Primary Examiner* — Philip R Wiest
*Assistant Examiner* — Benjamin Klein
(74) *Attorney, Agent, or Firm* — Bereskin & Parr LLP

(57) ABSTRACT

A kit of parts for an injection safety system comprises a vial comprising a container for storing an injectable substance, and an identifier removably secured to the container. The identifier comprises an indicium of the substance, and an engagement portion. The kit of parts further comprises a syringe for drawing the substance from the vial. The syringe comprises a mating engagement portion. The mating engagement portion is mateable with the engagement portion to secure the identifier to the syringe and transfer the identifier from the vial to the syringe.

24 Claims, 14 Drawing Sheets

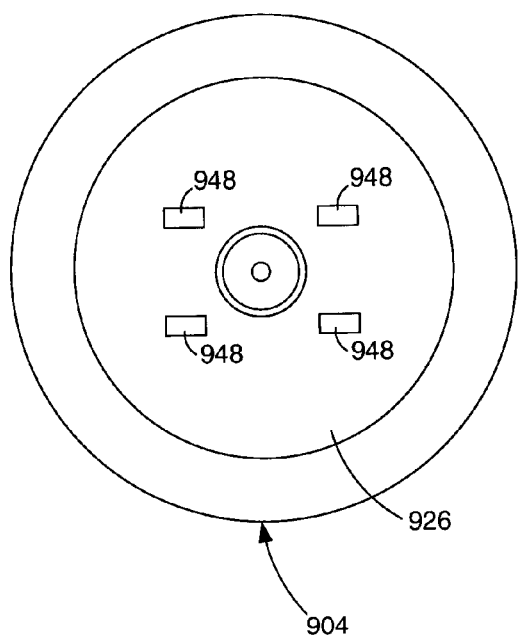
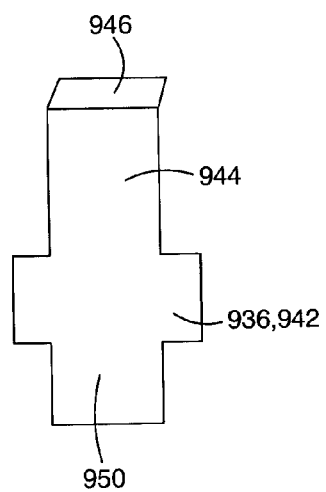
FIG. 9b
FIG. 9c

INJECTION SAFETY SYSTEM

CROSS REFERENCE TO RELATED APPLICATION

This application claims priority from U.S. Provisional Patent Application No. 61/316,088, filed Mar. 22, 2010, which is incorporated by reference herein in its entirety.

FIELD

The disclosure relates to an injection safety system. Specifically, the disclosure relates to an injection safety system for use when drawing a substance from a vial into a syringe.

INTRODUCTION

The following is not an admission that anything discussed below is prior art or part of the common general knowledge of persons skilled in the art.

U.S. Pat. No. 6,985,870 (Martucci) discloses a medication delivery system that comprises a medical container holding a prescribed medication to be delivered to a patient, a tag adapted to be worn by the patient, a handheld computing device, and an electronic medication delivery device. Data on the medication is contained in a first label on the medication container. The first label also contains the instruction on how the medication is delivered to the patient, including the appropriate settings for an electronic medication delivery device for delivering the medication to the patient. Patient data is contained in a second label on the tag worn by the patient. The medication data, medication delivery instruction, and patient data are provided in machine-readable formats. The handheld computing device reads the medication data and the medication delivery instruction on the medication container and the patient data on the patient tag. The handheld computing device stores the information obtained and performs a matching check to confirm that the medication data matches with the patient data. Upon a confirmed match, it transmits the medication delivery instruction to the electronic medication delivery device, which downloads the instruction, programs the delivery device, and prompts an operator to begin delivering the medication to the patient according to the downloaded instruction.

SUMMARY

The following summary is provided to introduce the reader to the more detailed discussion to follow. The summary is not intended to limit or define the claims.

According to one aspect, a kit of parts for an injection safety system is disclosed. The kit of parts comprises a vial comprising a container for storing an injectable substance, and an identifier removably secured to the container. The identifier comprises an indicium of the substance, and an engagement portion. The kit of parts further comprises a syringe for drawing the substance from the vial. The syringe comprises a mating engagement portion. The mating engagement portion is mateable with the engagement portion to secure the identifier to the syringe and transfer the identifier from the vial to the syringe.

The syringe may comprise a needle and a barrel in fluid communication with the needle. The mating engagement portion may be securable to the engagement portion when the needle is inserted into the vial.

When the needle is inserted into the vial to draw the substance from the vial, the identifier may be automatically transferred from the vial to the syringe. Alternately, manual assistance may be (or may not be in certain embodiments) required to remove the identifier from the vial.

The container may comprise a cap, and the cap may be the identifier. The cap may comprise an aperture extending therethrough, and an annular mount surrounding the aperture. The annular mount may define the engagement portion.

The kit of parts may further comprise a cover removably received on the aperture. The cover may comprise a label adhered to the cap over the aperture, and the label may be removable from the cap and adherable to the syringe.

The syringe may comprise (i) a needle and a fitting secured to the needle, and (ii) a barrel and a mating fitting secured to the barrel. The mating fitting may be mateable with the fitting for removably securing the needle in fluid communication with the barrel. The fitting may comprise the mating engagement portion.

The needle may be insertable into the vial via the aperture, and when the needle is inserted into the vial, the fitting may be received in the annular mount. When the fitting is received in the annular mount, the outer surface of the fitting may frictionally engage the annular mount to secure the cap to the fitting. When the fitting is removed from the aperture, the cap may be removed from the vial and may be retained on the fitting.

The indicium may comprise at least one of a color of the cap, a pattern on the cap, printing on the cap, and a label secured to the cap.

Upon insertion of the needle into the vial via the aperture, and prior to the needle's fitting becoming frictionally engaged with the annular mount, the force and area of the fitting being pushed into the aperture may cause a separation of a perforated material (e.g. metal breakable securing ring), whose purpose is to secure the cap to the vial until it is broken. The breaking of the perforated material may cause the cap to separate from the vial, and may allow the cap to become secured to the needle via frictional engagement of the fitting and annular mount—without the need for the cap to be manually separated from the vial.

The kit of parts may further comprise a second vial comprising a second container storing a second injectable substance, and a second identifier removably secured to the second container. The second identifier may comprise a second indicium of the second substance and a second engagement portion. The second engagement portion may be securable to the identifier such that when the needle is inserted into the second vial to draw the second substance from the vial, the second identifier is transferred from the second container to the syringe adjacent the first identifier.

According to another aspect, a vial for an injection safety system is provided. The vial comprises a container for storing an injectable substance, and an identifier removably secured to the container and comprising an indicium of the substance and an engagement portion. The engagement portion is mateable with a mating engagement portion of a syringe to secure the identifier to the syringe and transfer the identifier from the vial to the syringe.

The identifier may comprise a cap for the container. The cap may comprise an aperture extending therethrough, and an annular mount surrounding the aperture. The annular mount may define the engagement portion.

The vial may further comprise a cover removably received on the aperture. The cover may comprise a label adhered on the cap over the aperture. The label may be removable from the cap and adherable to the syringe.

The indicium may comprise at least one of a color of the cap, a pattern on the cap, printing on the cap, and a label removably secured to the cap.

A needle of the syringe may comprise a fitting, and the cap may be configured such that the needle is insertable into the vial via the aperture, and when the needle is inserted into the vial, the fitting is received in the aperture.

The mount may be configured to frictionally engage an outer surface of the fitting when the fitting is received in the aperture to secure the cap to the fitting.

The cap may be configured to be removed from the vial and retained on the fitting.

The identifier may be configured such that the engagement portion is mateable with the mating engagement portion when the needle is inserted into the vial.

The identifier may be configured such that when a needle of the syringe is inserted into the vial to draw the substance from the vial, the identifier is automatically transferred from the vial to the syringe. Alternately, the identifier may be automatically secured to the syringe, and manual assistance may be required to remove the identifier from the vial.

The identifier may be configured to automatically disengage itself from the vial and retained on the fitting, when the fitting is received in the aperture and pushed against a perforated material whose purpose is to secure the identifier to the vial. The pushing of the fitting against the perforated material (breakable securing ring) may cause the perforated material to separate, automatically disengaging the identifier from the vial. The fitting may still frictionally engage with the mount to permit adherence of the identifier to the syringe.

According to another aspect, a vial for an injection safety system is disclosed. The vial comprises a container for storing an injectable substance. The container comprises a body and a neck. A pierceable seal seals the neck. A cap is removably secured to the container over the seal. The cap comprises an indicium of the substance and an aperture defined transversely therethrough. A cover is removably secured to the cap over the aperture.

The vial may further comprise a breakable securing ring securing the cap to the seal.

According to another aspect, a method is disclosed for drawing an injectable substance into a syringe from a vial. The method comprises a) inserting a needle of the syringe into the vial, the vial having an identifier removably secured thereto; b) engaging the syringe with the identifier to secure the identifier to the syringe; and c) withdrawing the needle from the vial and removing the identifier from the vial.

Step (c) may comprise automatically or manually lifting the identifier off the vial, after insertion of the needle into the vial.

DRAWINGS

Reference is made in the detailed description to the accompanying drawings, in which:

FIG. 9b is a top plan view of the vial of FIG. 9a, after a label has been removed from the vial;

FIG. 9c is a top plan view of the label of FIG. 9a, after being removed from the vial;

DETAILED DESCRIPTION

Drug administration errors may occur when a patient is accidentally injected with the wrong substance. These errors can occur for several reasons. For example, in some fields of medicine, such as anesthesia, syringes are often pre-loaded with a drug, and then set aside for later use. For example, prior to a procedure, a syringe may be loaded with a drug, by drawing the drug into the syringe from a vial. The syringe may then be labeled with a paper label to indicate the particular drug that is in the syringe. This may be done for several different drugs. The syringe(s) may then be set aside for later use, during a procedure. In some instances, the syringe is labeled incorrectly. Accordingly, when the syringe is later used, the patient is injected with the wrong drug. Alternately, a user may later accidentally pick up the wrong syringe from a group of pre-loaded syringes, and thus the patient is injected with the wrong drug.

The present disclosure provides an injection safety system which may reduce the instances of a patient being injected with the wrong drug, or may minimize the risk of a patient being injected with the wrong drug.

Figure 1:
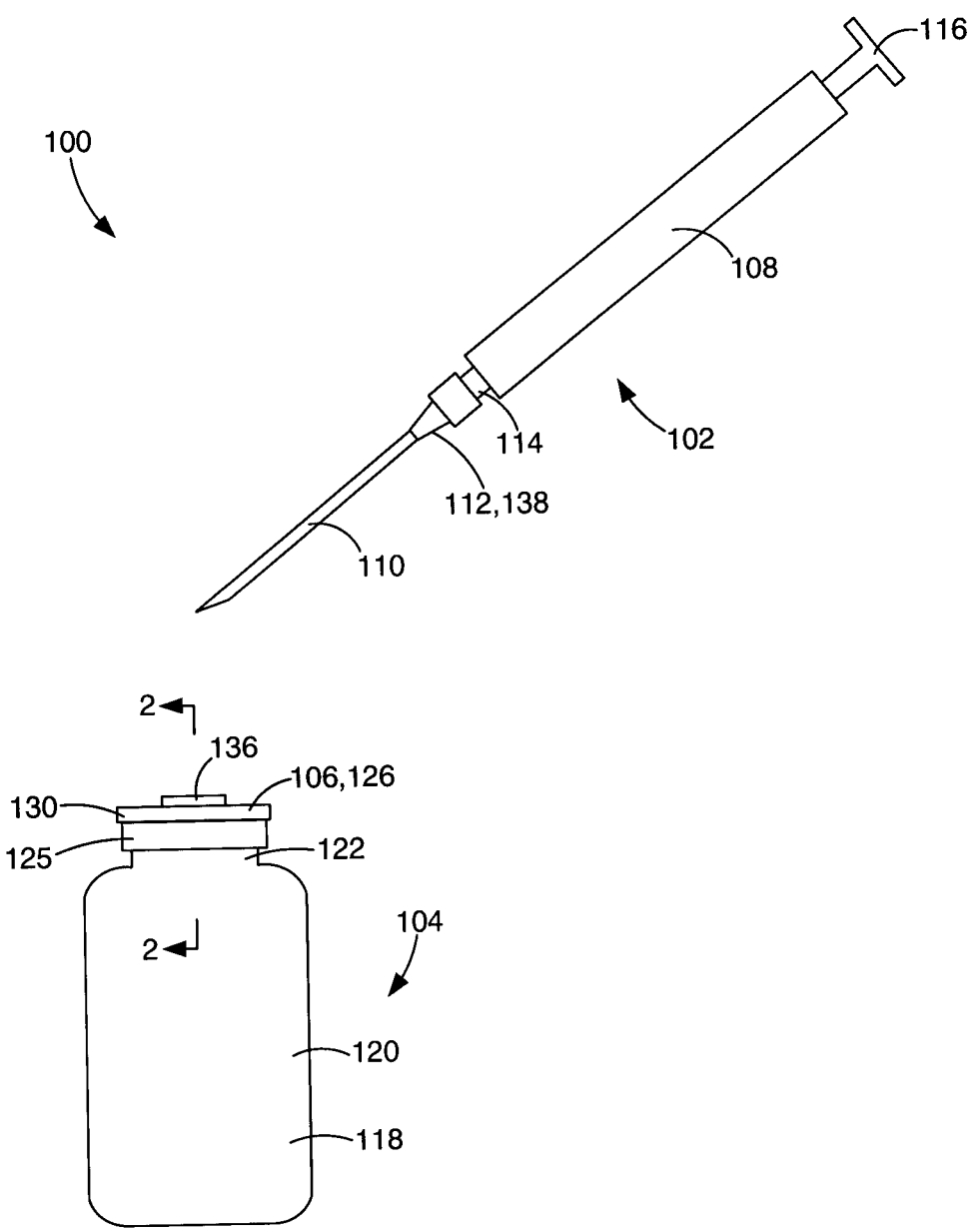
FIG. 1 is a plan view of an example of a kit of parts of an injection safety system, including a syringe and a vial.
Figure 5:
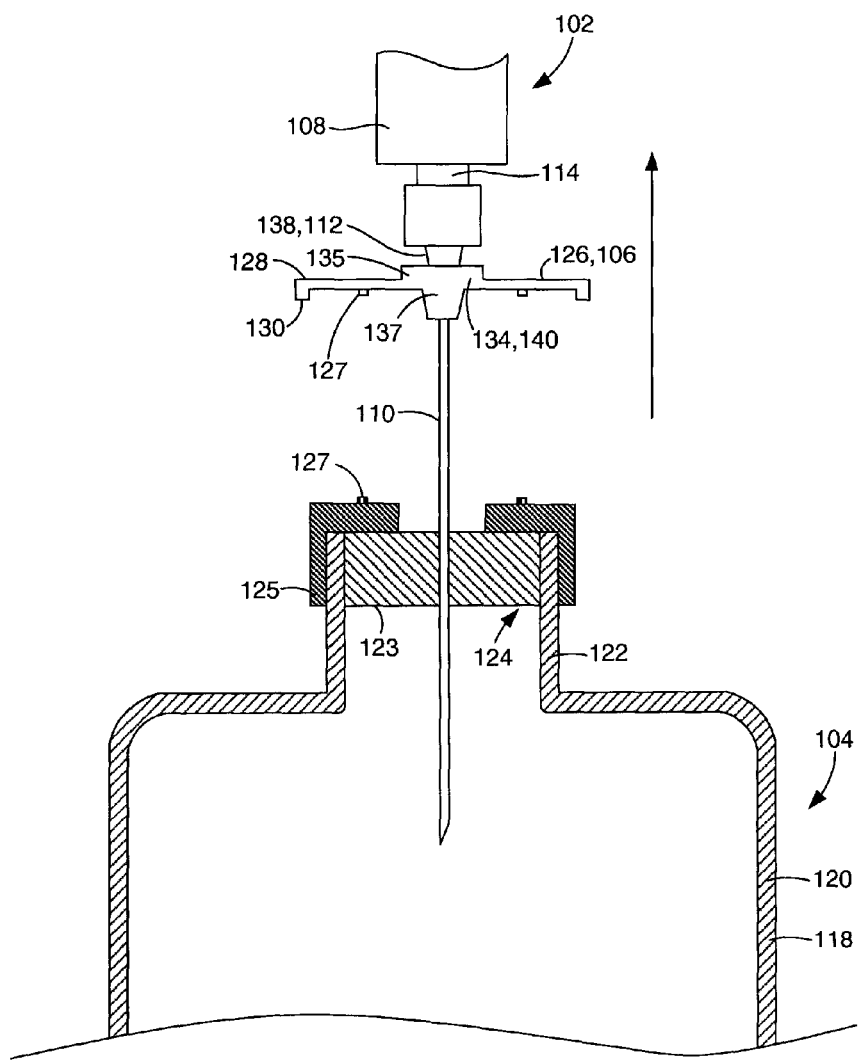
FIG. 5 shows the vial of FIG. 2, with the syringe of FIG. 1 shown in partial plan view and partially removed from the vial, with the cap of the vial shown in plan view and secured to the syringe.
Figure 6:
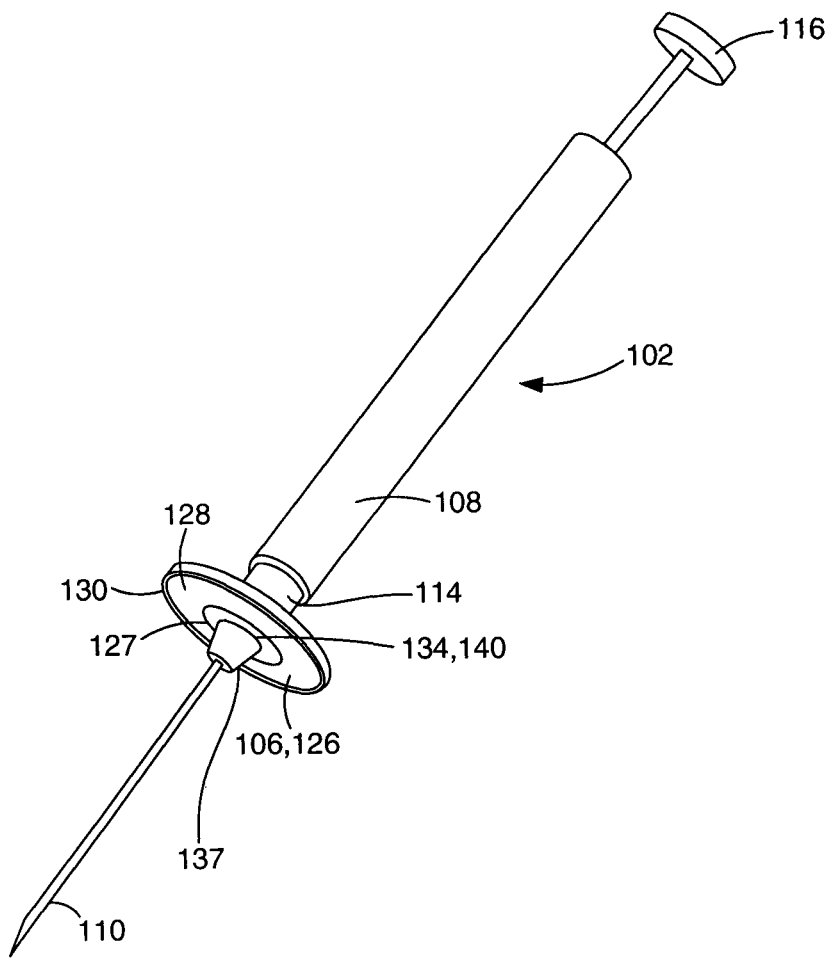
FIG. 6 is a perspective illustration of the syringe of FIG. 1, having the cap of the vial of FIG. 1 secured thereto.

Referring to FIG. 1, an exemplary kit of parts 100 for an injection safety system is shown. The kit of parts 100 comprises a syringe 102 and a vial 104. As will be described in further detail hereinbelow, the vial 104 comprises an identifier 106 that indicates the substance that is within the vial 104. The vial 104 and syringe 102 are configured such that when the syringe 102 is used to draw the substance from the vial 104, the identifier 106 is transferrable from the vial 104 to the syringe 102, as shown in FIGS. 5 and 6, so that the identifier 106 is then secured to the syringe 102. Accordingly, the syringe 102, when loaded with the substance from the vial 104, comprises the identifier 106, which now indicates the substance that is within the syringe 102.

Referring still to FIG. 1, in the example shown, the syringe 102 is a known syringe comprising a barrel 108, and a needle 110 in fluid communication with the barrel 108. A fitting 112 is secured to the needle 110, and a mating fitting 114 is secured to the barrel 108, for removably securing the needle 110 in fluid communication with the barrel 108. The fitting 112 and the mating fitting 114 may be removably secured together by friction. For example, the fitting 112 and the mating fitting 114 may be Luer-Slip fittings. Alternately, the fitting 112 and the mating fitting 114 may be Luer-Lok fittings. A plunger 116 is mounted to the barrel 108, for drawing liquid into the barrel 108 and expelling liquid from the barrel 108. For simplicity, the features of the syringe have not been shown in great detail. In alternate examples, a syringe for the kit of parts may be of another suitable design.

Figure 2:
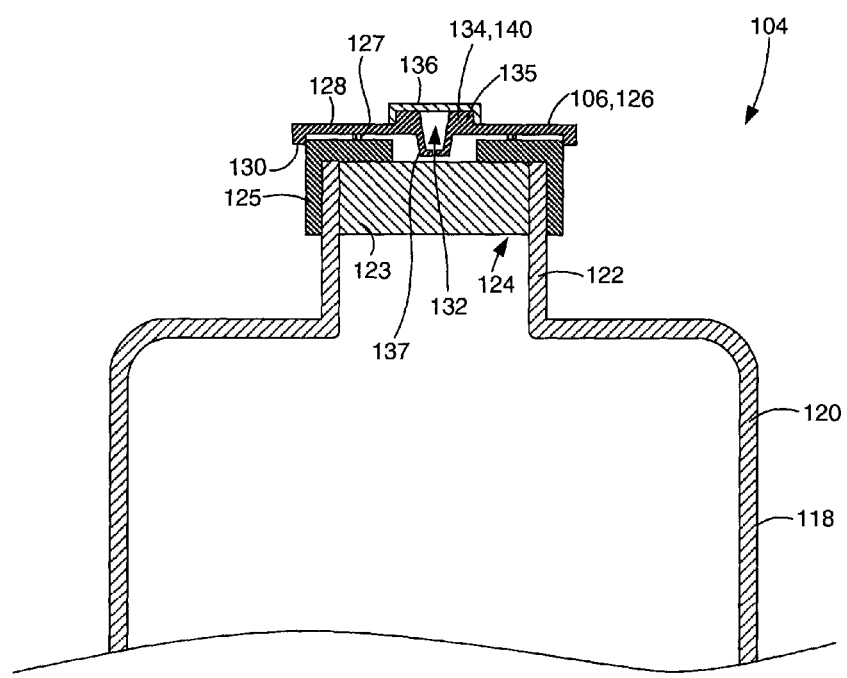
FIG. 2 is a cross section taken through the vial of FIG. 1, along line 2-2 in FIG. 1.

Referring to FIGS. 1 and 2, the vial 104 comprises a container 118 for storing an injectable substance. The injectable substance may comprise, for example, a drug or other substance such as a crystalloid or colloid solution or a vitamin. In the example shown, the container 118 is a known container comprising a body 120, and a neck 122. The container 118 may be, for example, made from glass or plastic. A pierceable seal 124 seals the neck 122. The seal 124 comprises a rubber disc 123 which is sealingly received in the neck 122, and an aluminum crimp 125 which secures the disc 123 within the neck 122, as is known in the art. In alternate examples, a container for the vial may be of another suitable design, and may not include a seal and crimp.

Referring still to FIGS. 1 and 2, as mentioned hereinabove, the vial 104 comprises an identifier 106 that indicates the substance that is within the vial 104. In the example shown, the vial 104 comprises a cap 126 for the container 118, and the cap 126 is the identifier 106. The identifier 106 comprises an indicium of the substance within the container 118. The indicium indicates to a user what the substance within the container 118 is. For example, the indicium may comprise a color of the cap 126, or a pattern on the cap 126. For example, the cap 126 may be fabricated from a plastic material of a particular color or pattern, and the particular color or pattern may be associated with a particular substance (standardized colors and their associated substances are known in the art). For example, vials with red caps may comprise a certain anesthetic, and vials with blue caps may comprise another anesthetic.

In alternate examples, the indicium may be another suitable type of indicium. For example, the indicium may comprise printing or embossing which lists the name of the substance, or a symbol associated with the substance. Alternately, the indicium may comprise a particular shape or size of cap associated with the substance. Alternately, the indicium may include an electronically readable indicium, such as a barcode or RFID or NFC tag.

Further, the indicium may also indicate additional information, such as a drug identification number, which may indicate the particular vial or batch that the substance came from.

Referring still to FIGS. 1 and 2, the cap 126 is secured to the neck 122 over the seal 124. In the example shown, the cap 126 comprises a planar portion 128, which is seated above the rubber disc 123, and a depending lip 130, which is received around the crimp 125. The lip 130 and the planar portion 128 may be, for example, made from a plastic. A securing ring 127 is secured between the planar portion 128 and the crimp 125, to secure the cap 126 to the crimp 125. The securing ring 127 is breakable, such that the cap 126 may be removed from the container 118 by lifting the lip 130 away from the crimp 125 to break the ring 127. For example, the securing ring 127 may be made from a metal foil that is adhered to the planar portion 128 and the crimp 125. When sufficient force is applied to lift the lip 130 away from the crimp 125, the foil may break. The securing ring 127 may also serve as a tamper evident feature, in that once it is broken, the cap 126 may not be able to be re-mounted to the container 118. In alternate examples, a cap for the container may be of another suitable design. For example, a cap may be screwed to the container, or frictionally mounted to the container.

As will be described in further detail, the vial 104 and the syringe 102 are configured such that the cap 126 is removable from the container 118, and is securable to the syringe 102, so that the syringe 102, when loaded with the substance from the vial 104, includes the identifier 106, which then indicates the substance within the barrel 108.

Figure 3:
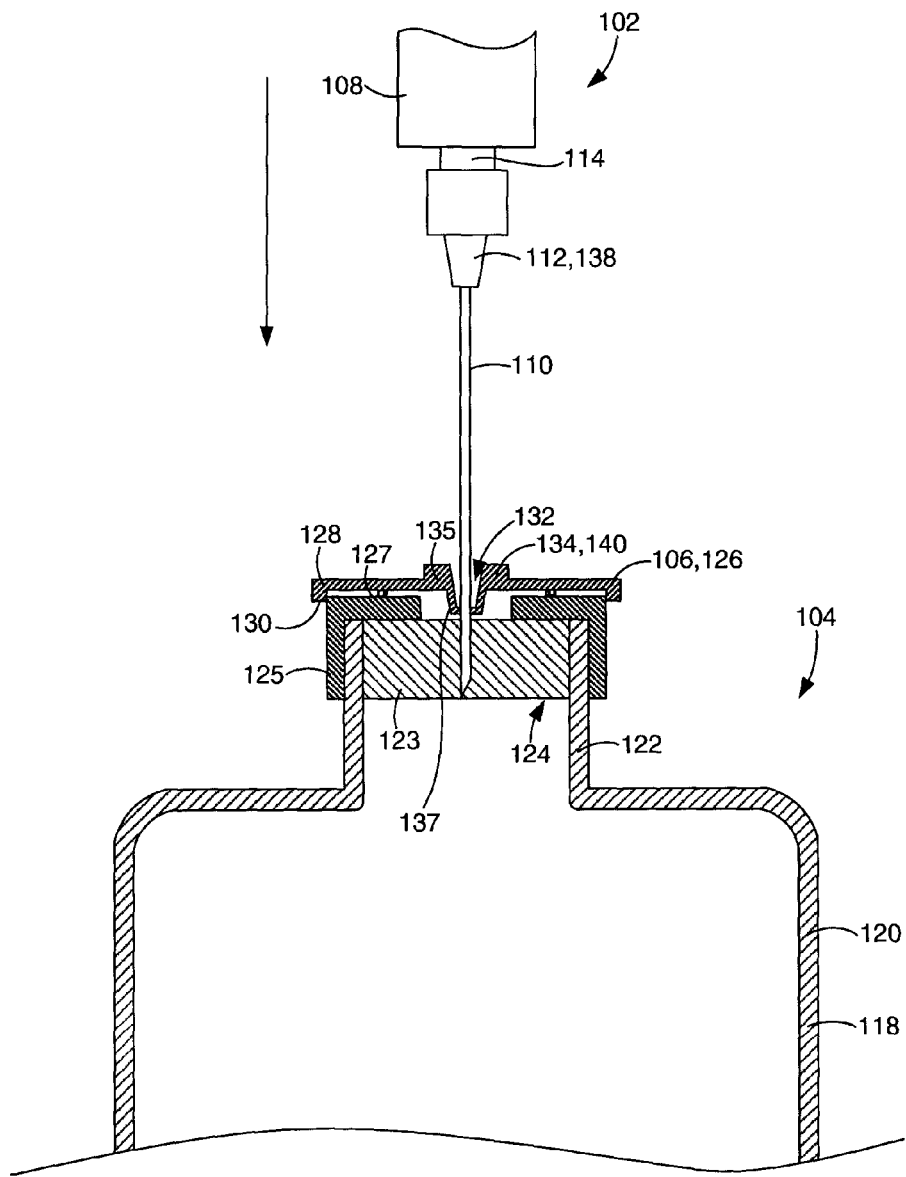
FIG. 3 shows the vial of FIG. 2, with the syringe of FIG. 1 shown in partial plan view and partially inserted into the vial.

Referring still to FIG. 2, the cap 126 has an aperture 132 extending therethrough. An annular mount 134 surrounds the aperture 132. The annular mount includes a body portion 135 and a depending rim 137. As exemplified, the annular mount is integral with the cap 126. However, in alternate examples, the annular mount 134 may be separately formed from the cap 126. The annular mount will be described in further detail hereinbelow. The vial 104 further comprises a cover 136 for the aperture 132. The cover 136 is removably secured to the cap 126 over the aperture 132. Particularly, as shown, the cover 136 is resiliently flexible and frictionally secured to the mount 134 over the aperture 132. Optionally, another breakable securing ring (not shown) may be provided between the cover 136 and the mount 134. Referring to FIG. 3, in use, the cover 136 may be removed from the cap 126, to expose the aperture 132. When the aperture 132 is exposed, the needle 110 may be inserted through the aperture 132 and through the septum 124 into the vial, as shown in FIG. 3.

Figure 4:
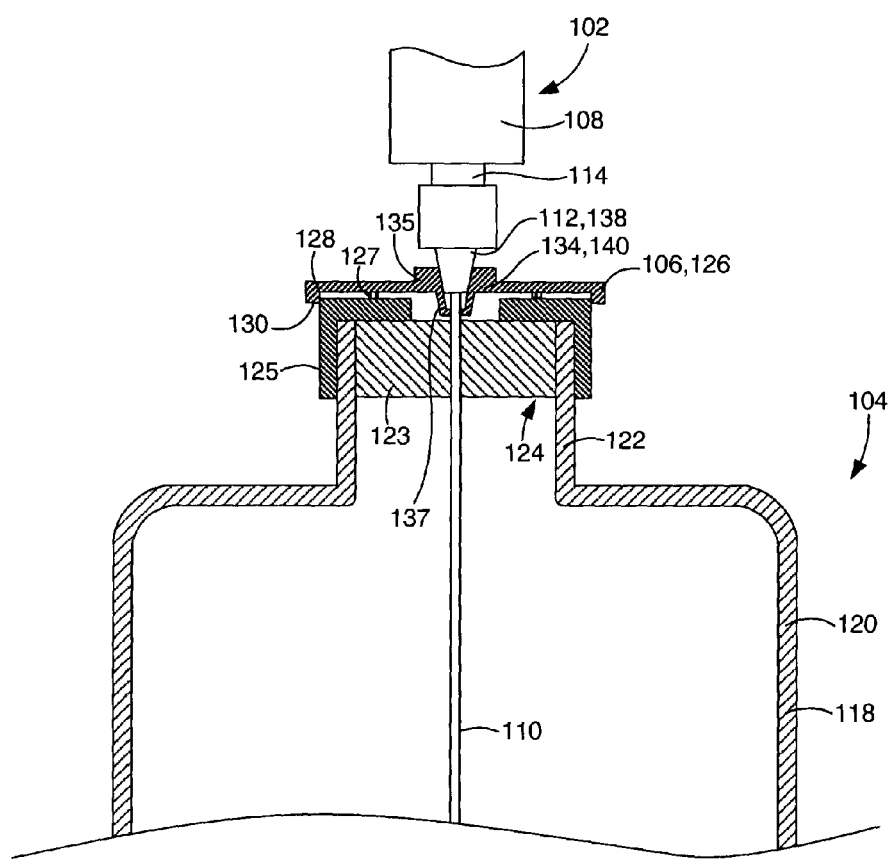
FIG. 4 shows the vial of FIG. 2, with the syringe of FIG. 1 shown in partial plan view fully inserted into the vial.

Referring still to FIG. 3, as the needle 110 is inserted through the aperture 132 and into the rubber disc 123, the fitting 112 of the syringe 102 will approach the mount 134. The mount 134, and particularly the body portion 135, serves as an engagement portion 140, which is mateable with a mating engagement portion 138 of the syringe 102, to secure the cap 126 to the syringe 102 and transfer the cap 126 from the vial 104 to the syringe 102. Particularly, referring to FIG. 4, the body portion 135 of the mount 134 is configured to receive the fitting 112 of the syringe 102 as the needle 110 of the syringe 102 is inserted into the septum 124, and to frictionally secure the cap 126 to the fitting 112. Particularly, in the example shown, as the needle 110 is inserted into the aperture 132, the fitting 112 will contact the body portion 135 of the mount 134. Additional force may then be applied, to force the fitting 112 further into the body portion 135 of the mount 134 and to frictionally secure the mount 134 to the fitting 112, as shown in FIG. 4.

When the fitting 112 is received in the mount 134, fluid may be drawn into the barrel 108 of the syringe 102, by withdrawing the plunger 116 away from the barrel 108.

Referring to FIG. 5, the needle 110 may then be removed from the vial 104. As mentioned hereinabove, the cap 126 is removably secured to the vial 104 by the securing ring 127. The securing ring 127 can be broken with manual pressure applied to the lip 130, in order to separate the cap 126 from the crimp 125. The needle 110 may then be removed from the vial, by pulling the barrel 108 away from the vial 104, as shown in FIG. 5. Due to frictional engagement between the fitting 112 and the mount 134, the cap 126 will be separated from the vial 104 and transferred to the syringe 102, as shown in FIG. 6.

In the example described above, manual assistance is required to break the securing ring 127 and thereby transfer the cap 126 to the syringe 102. In alternate examples, the cap 126 may be automatically transferred to the syringe 102, without manual assistance. For example the syringe 102 and vial 104 may be configured such that the force required to remove the fitting 112 from the mount 134 is greater than the force required to break the securing ring 127. Accordingly, when barrel 108 is pulled away from the vial 104, the securing ring 127 may break.

In the example shown, after the securing ring 127 has been manually broken to dissociate the cap 126 from the crimp 125, the cap 126 is automatically removed from the vial 104 and transferred to the syringe 102 when the needle 110 is withdrawn from the vial 104, due to the frictional engagement of the fitting 112 with the mount 134. In alternate examples, a user may also manually assist in removing the cap 126 from the vial 104, without having frictionally engaged the fitting 112 with the mount 134. For example, the cap 126 may initially be manually removed from the vial 104. The needle 110 may then be inserted through the rubber disc 123 to withdraw the contents of the vial 104. The needle 110 may then be withdrawn from the vial 104, and the cap 126 may then be manually secured to the syringe 102, by frictionally securing the mount 134 to the fitting 112.

The syringe 102 may then optionally be set aside for later use. When the syringe 102 is later picked up to be used, the cap 126 will remain on the syringe 102, and serves as an identifier 106 that will indicate to the user that a particular substance is within the barrel 108. When the syringe 102 is used to inject the substance into a patient, the identifier 106 may be viewed by the user, to check that the correct substance is injected. For example, a syringe 102 that has a red cap secured thereto may indicate that the syringe has a particular substance within the barrel 108. In addition, the cap 126 may also serve as a contamination barrier between the user of the syringe 102, and the object into which the syringe 102's contents are being injected into, or withdrawn from.

Figure 7:
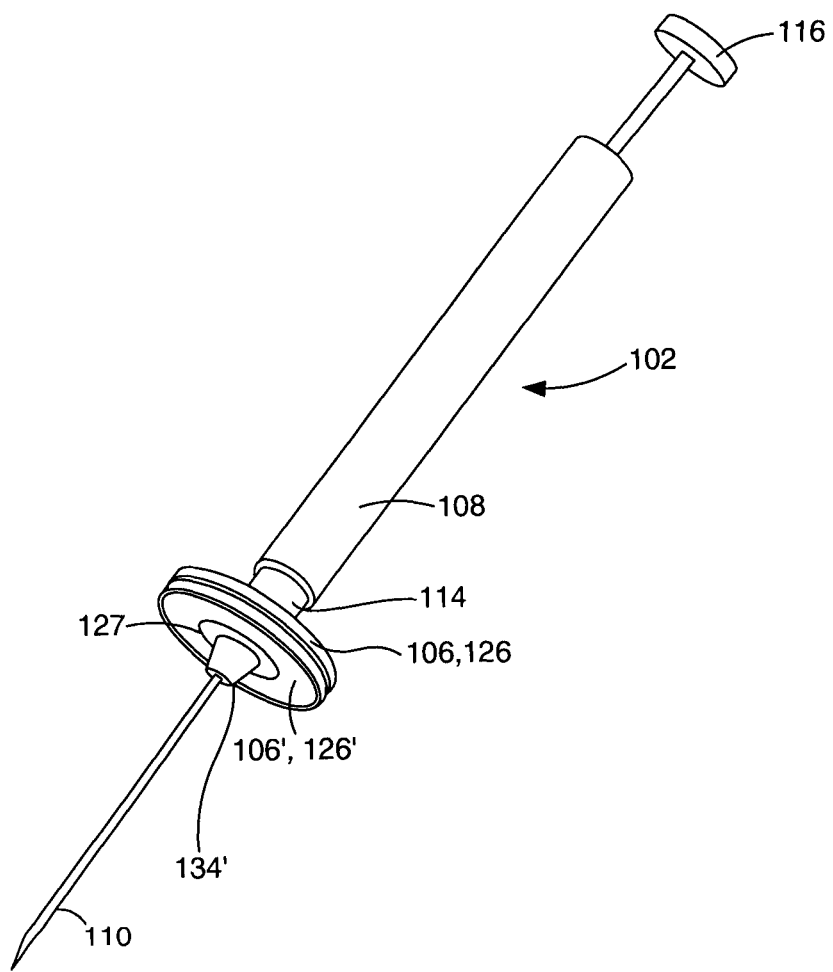
FIG. 7 is a perspective illustration of the syringe of FIG. 1, having two caps secured thereto.

Additionally, in some instances, it may be desired to draw a second substance into the syringe 102 (i.e. two substances may be mixed into one syringe). The second substance may be a different substance from the first substance, or the same substance but from a different vial. In such instances, after the syringe 102 has been used to draw the first substance into the barrel 108 and has the identifier 106 secured thereto, the needle 110 of the syringe 102 may be inserted into a second vial (not shown), so that a second identifier 106' of the second vial (i.e. a second cap 126' of the second vial) becomes secured thereto adjacent the first identifier 106, as shown in FIG. 7. Particularly, as mentioned hereinabove, the mount 134 of the cap 126 has a depending rim 137. The mount 134 is configured such that the depending rim 137 is frictionally receivable in the body portion (not shown) of the mount 134' of the second cap 126'. Accordingly, with the identifier 106 mounted to the syringe 102, the needle 110 of the syringe 102 may be inserted through the aperture (not shown) of the mount 134' of the second vial, until the depending rim 137 is received in and frictionally secured to the body portion of the mount 134'. The second substance may then be drawn into the syringe 102. A securing ring (not shown) of the second vial may then be broken, as described hereinabove, and the syringe may then be withdrawn from the second vial, with the second identifier 106' secured thereto. Accordingly, the syringe 102 will then have two identifiers 106, 106', secured thereto, respectively indicating the two substances that are within the barrel 108. This procedure may be repeated to permit the combination of even more than two substances.

In the example shown in FIG. 7, the second identifier 106' is secured to the syringe 102 indirectly, by the identifier 106 (i.e. the depending rim 137 of the identifier 106 is frictionally secured in the mount 134' of the second identifier 106'). In alternate examples, the second identifier 106' may be secured directly to the syringe 102, adjacent the first identifier 106.

As mentioned hereinabove, in some examples, the identifier 106, 106' may include a drug identification number. This may be particularly useful in examples where a second substance is drawn into the barrel 108, and the second substance is the same as the first substance. That is, the identifiers 106, 106' will indicate the vial or batch that the substances came from. This applies to additional substances drawn into the barrel 108 as well.

In the example shown, the fitting 112 is frictionally secured within the mount 134. In alternate examples, a fitting may be secured within a mount in another manner. For example, a mount may comprise one or more features that snapably mate a mating feature on the fitting. Alternately, a mount may comprise screw threads, and the outer surface of a fitting may comprise mating screw threads.

In the example shown, the annular mount 134 serves as an engagement portion 138 of the identifier 106, and the fitting 112 serves as a mating engagement portion 140 of the syringe 102. In alternate examples, an identifier and syringe may have alternate engagement portions. For example, an identifier may comprise a clip that is securable to the barrel of a syringe.

In the example shown, the cap 126 serves as the identifier 106 that is transferred from the vial 104 to the syringe 102. In alternate examples, an alternate identifier may be provided that is transferred from a vial to a syringe. For example, a separate identifier may be removably mounted to a vial, and may be manually or automatically transferred to a syringe when a needle is inserted into the vial.

Figure 8:
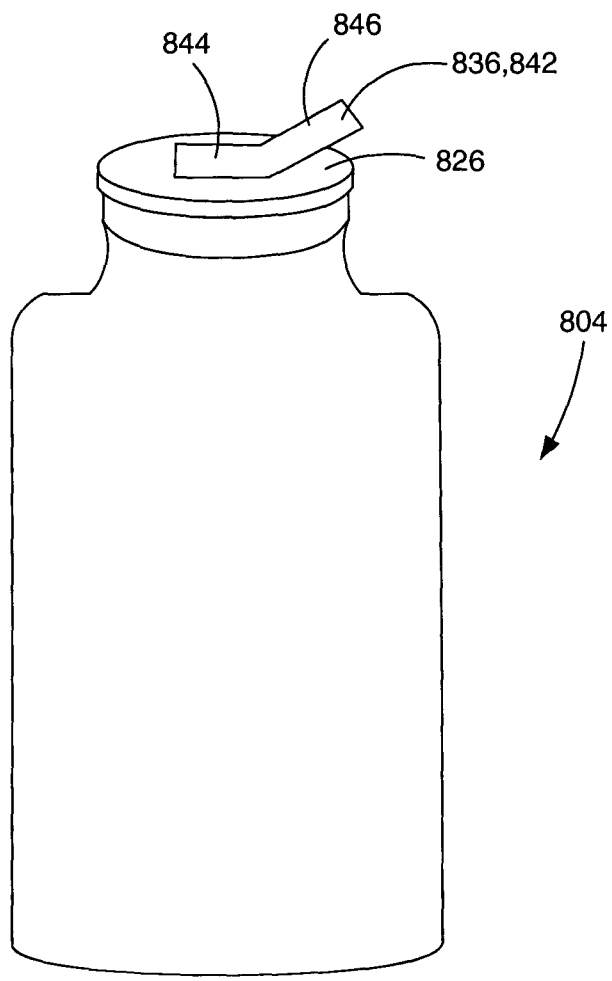
FIG. 8 is a perspective illustration of an alternate vial for a kit of parts for a drug safety system.

Referring now to FIG. 8, wherein like reference numerals are used to indicate like features as in FIGS. 1 to 7, with the first digit incremented to 8, an alternate vial 804 is shown. In the vial 804, the cover 836 for the aperture (not shown) is a label 842 that is adhered to the cap 826. The label 842 comprises an adhesive portion 844 that is adhered to the cap 826 over the aperture (not shown), and a tab portion 846 that extends from the adhesive portion 844. The length of the adhesive portion 844 may be extended and overlap the edge of the cap 826, to permit additional space on the label 842 for information to be printed. The label 842 may comprise a second indicium of the drug. For example, the tab portion 846 and/or adhesive portion 844 may be printed with the name of the drug, as well as other information. Additional information (e.g. drug concentration) may be written on the tab portion 846 and/or adhesive portion 844, with the use of a marking device. Alternately, the label may include an electronically readable indicium, such as a barcode or an RFID or NFC tag. In use, the label 842 may be removed from the vial 804, and adhered to the barrel of the syringe. The needle of the syringe may then be inserted through the aperture, and seal, so that the fitting engages the mount, and so that when the syringe is removed from the vial 804, the cap 826 is transferred to the syringe. Accordingly, in this example, the needle, when loaded with the substance from the vial 804, comprises two identifiers of the substance (i.e. the cap 826 and the label 842).

Figure 9A:
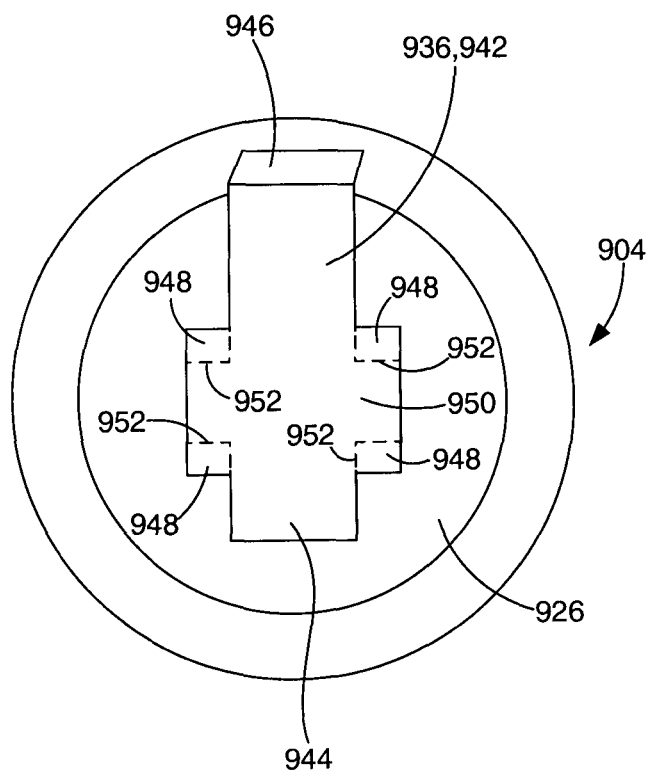
FIG. 9a is a top plan view of an alternate vial for a kit of parts for a drug safety system.

Referring now to FIGS. 9a to 9c, wherein like reference numerals are used to indicate like features as in FIGS. 1 to 7, with the first digit incremented to 9, an alternate vial 904 is shown. Referring to FIG. 9, similarly to the example of FIG. 8, in the vial 904, the cover 936 for the aperture is a label 942 that is adhered to the cap 926, and the label has a tab portion 946 and an adhesive portion 944. The adhesive portion 944 of the label 942 comprises removable portions 948 that are joined to the remainder 950 of the label 942 along perforated lines 952. In the example shown, the removable portions 948 are adhered to the cap 926. The remainder 950 of the label is not adhered to the cap 926 (i.e. is generally free of adhesive). The label 942 is configured such that when the label 942 is removed from the cap 926, the label 942 will tear along the perforated lines 952, so that the removable portions 948 remain adhered to the cap 926, as shown in FIGS. 9b and 9c. This serves as a tamper-evident feature. Particularly, after the label 942 has been torn, the remainder 950 of the label 942 may not be replaced back on the cap 926, as it is generally free of adhesive. Furthermore, even if it is attempted to adhere the remainder 950 back on the cap 926, the remainder 950 that is detached from removable portions 948 (due to the perforated lines 952) will be visible to a user, and will indicate to a user that the label 942 has been previously removed from the cap 926 (and thus, possibly indicate the presence of contamination).

Figure 10:
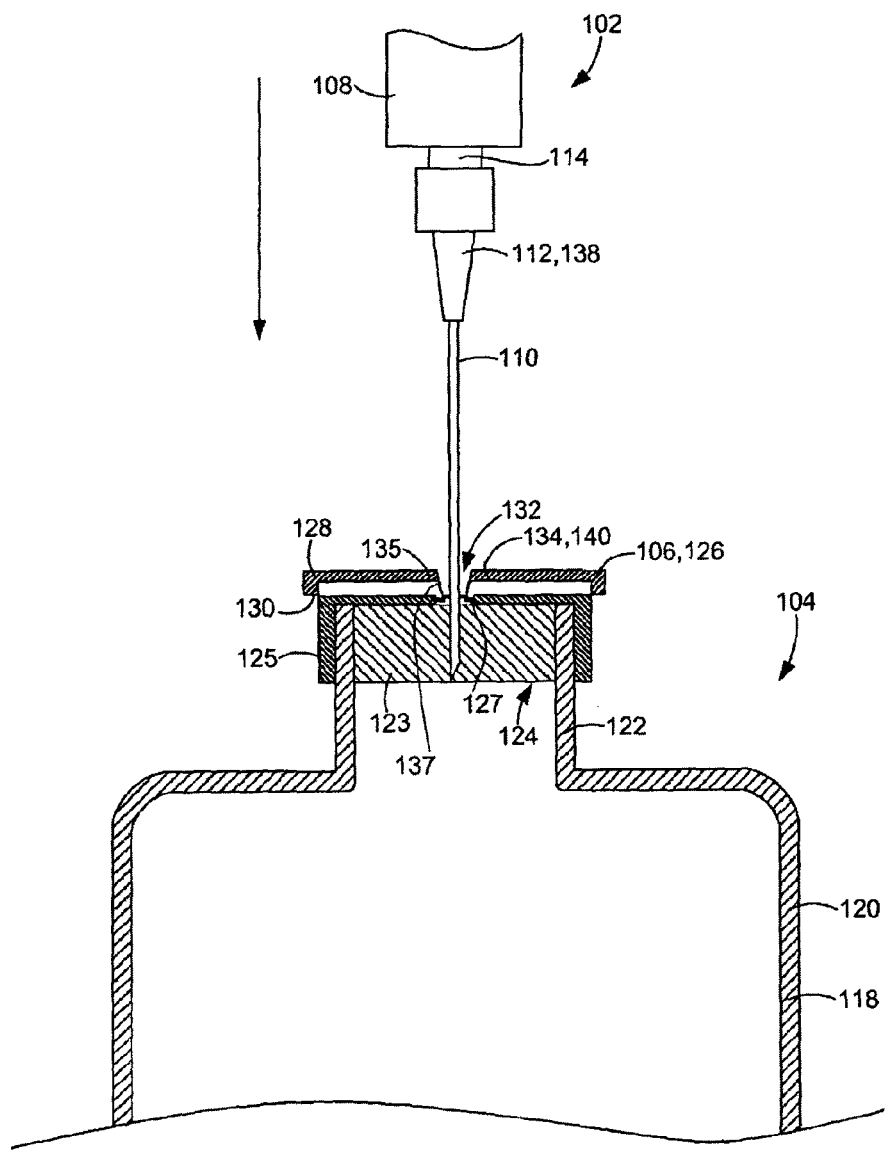
FIG. 10 shows the vial of FIG. 3 with a modified cap and a modified securing ring, along with a modified syringe of FIG. 1 shown in partial plan view and partially inserted into the vial.
Figure 11:
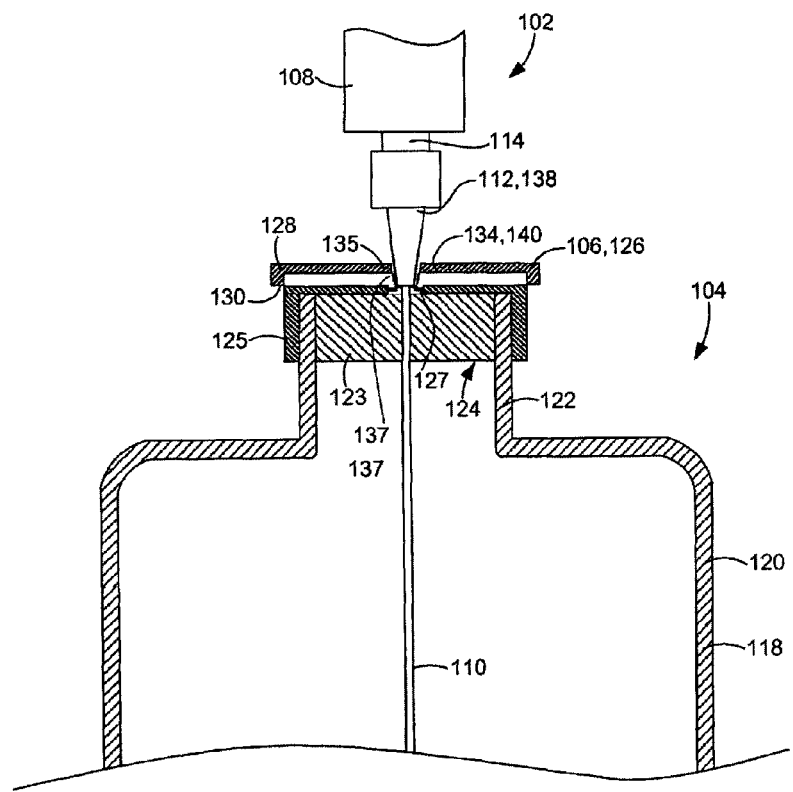
FIG. 11 shows the vial of FIG. 10, with the syringe of FIG. 10 shown in partial plan view almost fully inserted into the vial.
Figure 12:
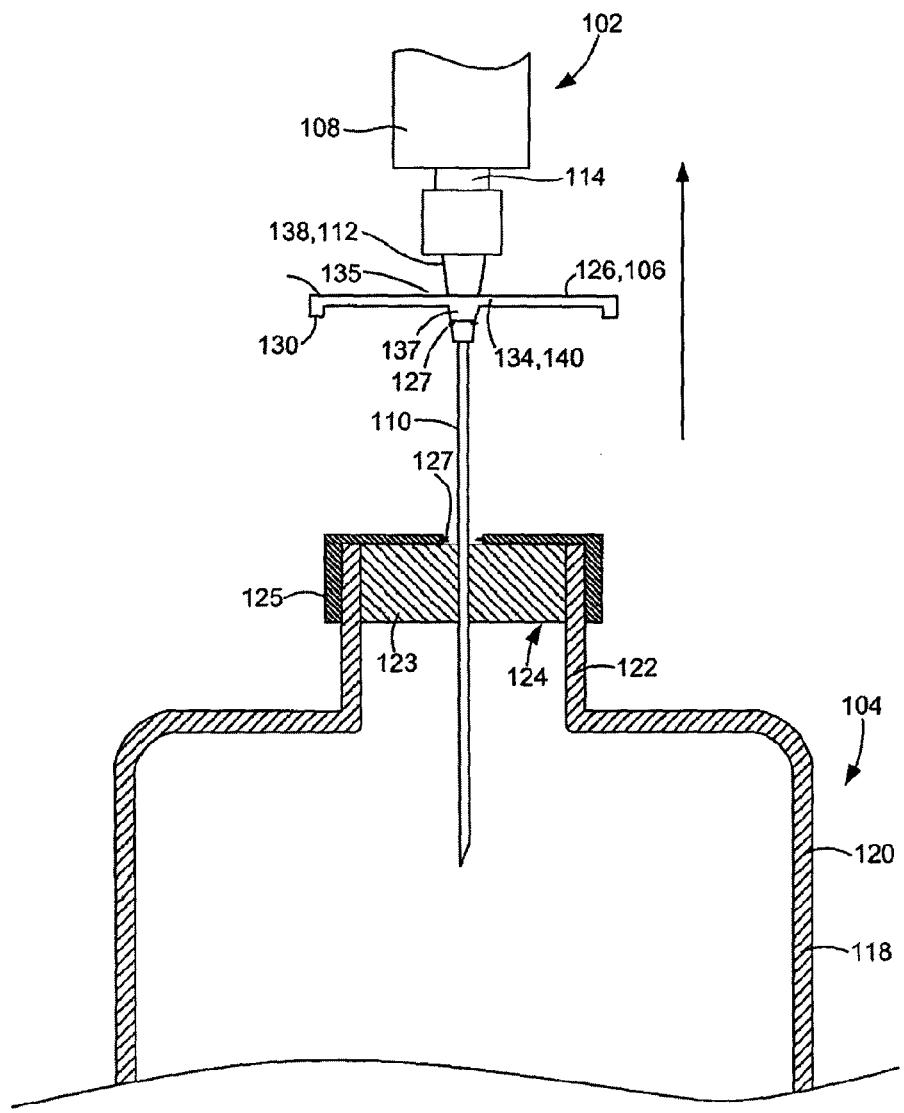
FIG. 12 shows the vial of FIG. 10, with the syringe of FIG. 10 shown in partial plan view and partially removed from the vial, with the cap of the vial shown in plan view and secured to the syringe.

Another example of automatically transferring the cap 126 to the syringe 102, without manual assistance, is shown serially in FIG. 10, FIG. 11, and FIG. 12. In these figures, a variety of potential modifications to the kit of parts 100 have been depicted. These modifications do not necessarily have to be simultaneously implemented in the kit of parts 100. These modifications include the absence of the body portion 135 of the mount 134, resulting in cap 126 having a planar surface instead of a protruding body portion 135; the aperture 132 will still be configured to receive the fitting 112 of the syringe 102. Additionally, the depending rim 137 has both been widened in diameter and narrowed in thickness, to increase the diameter of the aperture 132. The fitting 112 has been depicted as being elongated compared to its shape in FIGS. 1 to 7. Note that dimensions are not to scale. The securing ring 127 has been relocated to the central portion of the crimp 125, on top of the center of the rubber disc 123. The securing ring 127 directly secures the crimp 125 to the depending rim 137. When the needle 110 is introduced into the aperture 132 as shown in FIG. 11, the distal end of the fitting 112 will eventually contact the securing ring 127. With enough force applied to the syringe 102 towards the vial 104, the perforated securing ring 127 will be broken, leaving remnants of the securing ring 127 (the remnants are a detachable portion of the securing ring) on both the crimp 125 and on the depending rim 137. Further force applied to the syringe 102 towards the vial 104 will engage the fitting 112 with the mount 134, resulting in their frictional engagement. FIG. 12 shows the separation of the cap 126 from the vial 104 and transferred to the syringe 102, after the syringe 102 is pulled away from the vial 104.

Figure 13:
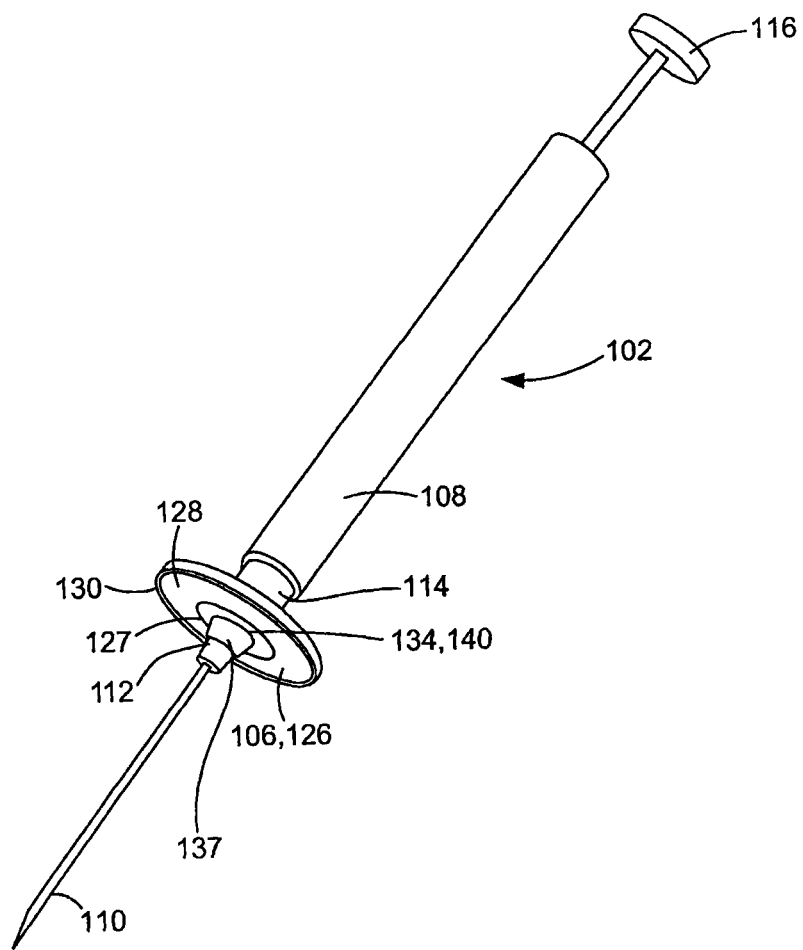
FIG. 13 is a perspective illustration of the syringe of FIG. 10, having the cap of the vial of FIG. 10 secured thereto.

FIG. 13 shows the appearance of the syringe 102 with the frictionally engaged cap 126, based on the modifications shown in FIGS. 10 to 12. FIG. 13 is identical to FIG. 6, with the exception of the absence of the body portion 135 (not visible) of the mount 134, as well as the protrusion of the fitting 112 beyond the distal portion of the depending rim 137. Additional identifiers, such as 106 and 106' on syringe 102 seen in FIG. 7, may be applied in the same manner to the syringe 102 seen in FIG. 13, through the mechanism depicted in FIGS. 10 to 12 using a second vial. Again, the only difference will be the absence of the body portion 135 of the mount 134, as well as the protrusion of the fitting 112 beyond the distal portion of the depending rim 137' from the cap 126' of the second vial.

Various apparatuses or methods have been described to provide an example of each claimed invention. No example described limits any claimed invention and any claimed invention may cover processes or apparatuses that are not described. The claimed inventions are not limited to apparatuses or processes having all of the features of any one apparatus or process described or to features common to multiple or all of the apparatuses described. It is possible that an apparatus or process described is not an embodiment of any claimed invention. Applicant reserves the right to claim such apparatuses or processes in other applications.

The invention claimed is:

1. A kit of parts for an injection safety system, the kit of parts comprising:
    a) a vial comprising a container for storing an injectable substance, and an identifier removably secured to the container, the identifier comprising an indicium of the substance and an engagement portion; and
    b) a syringe for drawing the substance from the vial, the syringe comprising a mating engagement portion, the mating engagement portion mateable with the engagement portion to secure the identifier to the syringe and transfer the identifier from the vial to the syringe;
wherein the vial comprises a cap, and the cap is the identifier; and
wherein the cap comprises an aperture extending therethrough, and a mount surrounding the aperture, the mount defining the engagement portion.

2. The kit of parts of claim 1, wherein the syringe comprises a needle and a barrel in fluid communication with the needle, and the mating engagement portion is securable to the engagement portion when the needle is inserted into the vial.

3. The kit of parts of claim 1, further comprising a cover removably received on the aperture.

4. The kit of parts of claim 3, wherein the cover comprises a label adhered to the cap over the aperture, and the label is removable from the cap and adherable to the syringe.

5. The kit of parts of claim 1, wherein the syringe comprises (i) a needle and a fitting secured to the needle, and (ii) a barrel and a mating fitting secured to the barrel, the mating fitting mateable with the fitting for removably securing the needle in fluid communication with the barrel.

6. The kit of parts of claim 5, wherein the fitting comprises the mating engagement portion.

7. The kit of parts of claim 6, wherein the needle is insertable into the vial via the aperture, and when the needle is inserted into the vial, the fitting is received in the mount.

8. The kit of parts of claim 7, wherein when the fitting is received in the mount, the outer surface of the fitting frictionally engages the mount to secure the cap to the fitting.

9. The kit of parts of claim 8 wherein when the fitting is removed from the aperture, the cap is removed from the vial and is retained on the fitting.

10. The kit of parts of claim 1, wherein the indicium comprises at least one of a color of the cap, a pattern on the cap, printing on the cap, embossing on the cap, and a label secured to the cap.

11. The kit of parts of claim 1, further comprising: a second vial comprising a second container storing a second injectable substance, and a second identifier removably secured to the second container, the second identifier comprising a second indicium of the second substance and a second engagement portion.

12. The kit of parts of claim 11, wherein the second engagement portion is securable to the identifier such that when the needle is inserted into the second vial to draw the second substance from the vial, the second identifier is transferred from the second container to the syringe adjacent the first identifier.

13. A vial for an injection safety system, the vial comprising:
    a) a container for storing an injectable substance; and
    b) an identifier removably secured to the container and comprising an indicium of the substance and an engagement portion, the engagement portion mateable with a mating engagement portion of a syringe to secure the identifier to the syringe and transfer the identifier from the vial to the syringe;

wherein the identifier comprises a cap for the container; and wherein the cap comprises an aperture extending therethrough, and a mount surrounding the aperture, and the mount defines the engagement portion.

14. The vial of claim 13, further comprising a cover removably received on the aperture.

15. The vial of claim 14, wherein the cover comprises a label adhered on the cap over the aperture, and the label is removable from the cap and adherable to the syringe.

16. The vial of claim 13, wherein the indicium comprises at least one of a color of the cap, a pattern on the cap, printing on the cap, embossing on the cap, and a label secured to the cap.

17. The vial of claim 13, wherein a needle of the syringe comprises a fitting, the cap is configured such that the needle is insertable into the vial via the aperture, and when the needle is inserted into the vial, the fitting is received in the aperture.

18. The vial of claim 17, wherein the mount is configured to frictionally engage an outer surface of the fitting when the fitting is received in the aperture to secure the cap to the fitting.

19. The vial of claim 18, wherein the cap is configured to be removed from the vial and retained on the fitting when the fitting is withdrawn from the vial.

20. The vial of claim 17, wherein the identifier is configured such that the engagement portion is mateable with the mating engagement portion when the needle is inserted into the vial.

21. The vial of claim 13, wherein the identifier is configured such that when a needle of the syringe is inserted into the vial to draw the substance from the vial, the identifier is automatically secured to the syringe, and manual assistance required to remove the identifier from the vial.

22. A vial for an injection safety system, the vial comprising:
   a) a container for storing an injectable substance, the container comprising a body and a neck;
   b) a pierceable seal sealing the neck;
   c) a cap removably secured over the seal, the cap comprising an indicium of the substance, an aperture defined transversely therethrough, and a mount defining an engagement portion that is mateable with a mating engagement portion of a syringe to secure the mount to the syringe and transfer the mount from the vial to the syringe; and
   d) a cover removably secured to the cap over the aperture.

23. The vial of claim 22, further comprising a breakable securing ring securing the cap to the seal.

24. A vial for an injection safety system, the vial comprising:
   a) a container for storing an injectable substance;
   b) a cap secured to the container, the cap comprising an indicium of the substance, an aperture defined transversely therethrough, and a mount defining an engagement portion that is mateable with a mating engagement portion of a syringe to secure the mount to the syringe and transfer the mount from the vial to the syringe, wherein the mount engages the mating engagement portion when the syringe is received in the aperture, to secure the mount to the syringe.

* * * * *